(12) United States Patent
Suddaby

(10) Patent No.: US 11,583,326 B2
(45) Date of Patent: Feb. 21, 2023

(54) FUSION DEVICE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 255 days.

(21) Appl. No.: 17/062,102

(22) Filed: Oct. 2, 2020

(65) Prior Publication Data

US 2021/0228363 A1 Jul. 29, 2021

Related U.S. Application Data

(63) Continuation-in-part of application No. 16/774,079, filed on Jan. 28, 2020, now Pat. No. 11,172,969.

(51) Int. Cl.
*A61B 17/86* (2006.01)
*A61F 2/30* (2006.01)

(52) U.S. Cl.
CPC ............ *A61B 17/8625* (2013.01); *A61F 2/30* (2013.01); *A61F 2002/3055* (2013.01); *A61F 2002/30622* (2013.01); *A61F 2002/30845* (2013.01); *A61F 2002/30851* (2013.01); *A61F 2002/30995* (2013.01)

(58) Field of Classification Search
CPC ... A61B 17/86; A61B 17/8625; A61B 17/863; A61B 17/8635; A61B 17/864; A61B 17/8645; A61B 17/8665; A61B 2017/8655
See application file for complete search history.

(56) References Cited

U.S. PATENT DOCUMENTS

| | | | | |
|---|---|---|---|---|
| 4,175,555 A | | 11/1979 | Herbert | |
| 5,098,435 A | * | 3/1992 | Stednitz | A61B 17/1637 606/907 |
| 5,478,342 A | * | 12/1995 | Kohrs | A61B 17/8685 606/310 |
| 5,759,184 A | * | 6/1998 | Santangelo | A61B 17/742 606/313 |
| 5,849,004 A | * | 12/1998 | Bramlet | A61B 17/0401 606/310 |
| 6,030,162 A | | 2/2000 | Huebner | |

(Continued)

FOREIGN PATENT DOCUMENTS

| | | |
|---|---|---|
| CA | 2390912 | 1/2008 |
| EP | 3123970 | 2/2017 |
| FR | 2971138 | 8/2012 |

OTHER PUBLICATIONS

Rialto SI Fusion System Brochure, "A Unique Approach to Sacroiliac Joint Fusion Procedures", Medtronic, 2016.
(Continued)

*Primary Examiner* — Eric S Gibson
(74) *Attorney, Agent, or Firm* — Harter Secrest & Emery LLP; Michael Nicholas Vranjes

(57) ABSTRACT

A fusion device assembly for fusion of a joint, including a first screw portion, including a first distal end, a first proximal end, a first radially outward facing surface, and a first hole, a second screw portion, including a second distal end, a second proximal end, and a second radially outward facing surface, and a section, including a first end slidably engaged with the first hole, a second end non-rotatably secured to the second distal end, and a third radially outward facing surface.

19 Claims, 7 Drawing Sheets

(56) References Cited

U.S. PATENT DOCUMENTS

| | | | |
|---|---|---|---|
| 6,183,474 B1* | 2/2001 | Bramlet | A61B 17/1659 606/65 |
| 7,708,738 B2* | 5/2010 | Fourcault | A61B 17/863 606/67 |
| 7,780,710 B2* | 8/2010 | Orbay | A61B 17/8061 606/310 |
| 8,475,505 B2 | 7/2013 | Nebosky et al. | |
| 8,579,947 B2 | 11/2013 | Wu | |
| 8,617,226 B2* | 12/2013 | Kim | A61B 17/864 606/310 |
| 8,945,193 B2* | 2/2015 | Kirschman | A61B 17/8841 606/317 |
| 8,992,587 B2* | 3/2015 | Kirschman | A61B 17/7064 606/305 |
| 9,295,488 B2 | 3/2016 | Asfora | |
| 9,308,035 B2* | 4/2016 | Biedermann | A61B 17/744 |
| 9,358,056 B2 | 6/2016 | Stalcup et al. | |
| 9,358,057 B1 | 6/2016 | Whipple et al. | |
| 9,480,520 B2 | 11/2016 | Rampersaud et al. | |
| 9,526,547 B2* | 12/2016 | Reed | A61B 17/863 |
| 9,668,781 B2 | 6/2017 | Stark | |
| 9,833,321 B2 | 12/2017 | Rindal et al. | |
| 9,931,141 B2 | 4/2018 | Jimenez | |
| 10,172,656 B1* | 1/2019 | Reimels | A61B 17/844 |
| 10,251,688 B2 | 4/2019 | Asfora | |
| 10,499,969 B2* | 12/2019 | McGirt | A61B 17/8605 |
| 10,864,029 B2* | 12/2020 | Redmond | A61B 17/8685 |
| 11,172,969 B2* | 11/2021 | Suddaby | A61B 17/844 |
| 2002/0049447 A1* | 4/2002 | Li | A61B 17/68 606/313 |
| 2002/0143401 A1* | 10/2002 | Michelson | A61F 2/446 623/17.16 |
| 2002/0169453 A1* | 11/2002 | Berger | A61B 17/60 606/295 |
| 2003/0014054 A1 | 1/2003 | Huebner | |
| 2003/0078584 A1 | 4/2003 | Tipirneni | |
| 2003/0158557 A1* | 8/2003 | Cragg | A61B 17/1757 606/86 R |
| 2005/0177158 A1* | 8/2005 | Doubler | A61B 17/7225 606/66 |
| 2007/0233123 A1* | 10/2007 | Ahmad | A61B 17/864 606/307 |
| 2008/0009861 A1* | 1/2008 | Stark | A61F 2/4601 606/914 |
| 2010/0057141 A1* | 3/2010 | Abdelgany | A61B 17/8685 606/301 |
| 2011/0213426 A1* | 9/2011 | Yedlicka | A61B 17/864 606/309 |
| 2013/0018427 A1 | 1/2013 | Pham et al. | |
| 2013/0123857 A1* | 5/2013 | Biedermann | A61B 17/84 606/303 |
| 2013/0310883 A1* | 11/2013 | Levy | A61B 17/863 606/313 |
| 2013/0317503 A1 | 11/2013 | Yalizis | |
| 2014/0058460 A1* | 2/2014 | Reed | A61B 17/863 606/301 |
| 2014/0094859 A1* | 4/2014 | Reed | A61B 17/863 606/315 |
| 2014/0121707 A1 | 5/2014 | Stark | |
| 2014/0243912 A1* | 8/2014 | Mobasser | A61B 17/8635 606/311 |
| 2014/0257412 A1 | 9/2014 | Patty et al. | |
| 2014/0277186 A1 | 9/2014 | Granberry et al. | |
| 2015/0201979 A1* | 7/2015 | Paul | A61B 17/7233 606/62 |
| 2016/0242820 A1* | 8/2016 | Whipple | A61B 17/8685 |
| 2016/0287301 A1* | 10/2016 | Mehl | A61B 17/8685 |
| 2017/0196608 A1 | 7/2017 | Castaneda et al. | |
| 2017/0296245 A1* | 10/2017 | Gault | A61B 17/864 |
| 2017/0296344 A1 | 10/2017 | Souza et al. | |
| 2018/0055551 A1* | 3/2018 | Yalizis | A61B 17/7225 |
| 2018/0116814 A1 | 5/2018 | Sullivan et al. | |
| 2018/0153698 A1 | 6/2018 | Rindal et al. | |
| 2018/0235670 A1 | 8/2018 | Jimenez | |
| 2019/0125371 A1* | 5/2019 | Asfora | A61B 17/864 |
| 2019/0125408 A1* | 5/2019 | Asfora | A61B 17/8625 |
| 2019/0231405 A1* | 8/2019 | Redmond | A61B 17/8625 |
| 2019/0231406 A1 | 8/2019 | Asfora | |
| 2019/0388131 A1* | 12/2019 | Mehl | A61B 17/7055 |
| 2020/0038070 A1* | 2/2020 | Suddaby | A61F 2/4405 |
| 2020/0046413 A1* | 2/2020 | Thornes | A61B 17/863 |
| 2021/0228250 A1* | 7/2021 | Suddaby | A61B 17/869 |
| 2021/0228363 A1* | 7/2021 | Suddaby | A61F 2/30 |

OTHER PUBLICATIONS

Sicure® Sacroiliac Joint Fusion System Brochure, Alevio, LLC, Birmingham, AL, 2019.
www.spinemarketgroup@gmail.com, last accessed Apr. 15, 2020.
Acutrak 2® Headless Compression Screw System, Surgical Technique Guide Brochure, 2012 Acumed®, Hillsboro, OR, www.acumed.net, last accessed Apr. 15, 2020.

* cited by examiner

FUSION DEVICE

CROSS-REFERENCE TO RELATED APPLICATIONS

This application is filed under 35 U.S.C. § 120 as a continuation-in-part of U.S. patent application Ser. No. 16/774,079, filed on Jan. 28, 2020, which application is hereby incorporated by reference in its entirety.

FIELD

The present disclosure relates to orthopedic surgery, and more particularly to interbone fixation fusion devices and especially interarticular joint fixation, specifically deep tissue joints such as spinal facet joints and sacroiliac (SI) joints.

BACKGROUND

Fusion of spinal elements has been a long-standing solution to symptoms of degenerating spinal discs. In fact, even though artificial discs have made some progress in the surgical arena, spinal fusion remains the most reliable means of alleviating symptoms referable to degenerating discs and is still the de facto gold standard.

One of the consequences of spinal fusion is adjacent level degeneration. Even though a normal functional spinal segment is fused, spinal motion must still occur, with forces being transferred to adjacent normal segments placing them under increases stress and contributing to a more rapid degenerative decline.

Since most spinal fusions are done in the low back and include the sacrum, which fuses naturally after birth, caudally transferred forces are dispersed to the sacroiliac (SI) joints causing abnormal stresses upon these joints.

While cranially transmitted forces simply go to the disc above, which can be fused by traditional means of interbody and/or posterolateral fusion, the SI joint is unique, complex, and difficult to visualize with traditional fluoroscopic methods.

Successful spinal fusions are often plagued after months or years of successful relief of symptomatology by a return of symptoms due to adjacent level degeneration. As many as twenty-five percent (25%) of cases of recurrent pain post spinal fusion are felt to be secondary to increased and abnormal motion at the level of the SI joint which can be severe.

While SI joint fusion procedures have been around for many years, recent trends have focused on minimally invasive ways to stabilize the joint thereby alleviating pain caused by the abnormal stresses placed upon them through natural degeneration or accelerated degeneration caused by spinal fusion. The addition of computerized guidance systems to the operating room armamentarium has afforded additional ways that stabilization of complex and deep-seated joints can be achieved surgically.

Thus, there is a long-felt need for a fusion device that allows fusion of deep-seated joints by way of minimally invasive surgery.

SUMMARY

According to aspects illustrated herein, there is provided a fusion device assembly for fusion of a joint, comprising a first screw portion, including a first distal end, a first proximal end, a first radially outward facing surface, and a first hole, a second screw portion, including a second distal end, a second proximal end, and a second radially outward facing surface, and a section, including a first end slidably engaged with the first hole, a second end non-rotatably secured to the second distal end, and a third radially outward facing surface.

In some embodiments, the first screw portion further comprises threading arranged on the first radially outward facing surface, at least one flute extending from the first distal end to the first proximal end, and at least one cutting edge operatively arranged to cut through bone. In some embodiments, the first screw portion comprises a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction. In some embodiments, the second screw portion further comprises threading arranged on the second radially outward facing surface. In some embodiments, the second screw portion further comprises a head non-rotatably connected to the second proximal end. In some embodiments, the fusion device assembly further comprises a second hole extending through the second screw portion and the section. In some embodiments, the fusion device assembly further comprises a rod operatively arranged to extend through the second hole and engage the first screw portion. In some embodiments, when the rod is displaced in a first circumferential direction, one of the first screw portion and the second screw portion is displaced relative to the other of the first screw portion and the second screw portion. In some embodiments, when the rod is displaced in a first circumferential direction the second screw portion and the section are displaced in a axial direction toward the first screw portion. In some embodiments, the first screw portion comprises a first diameter, the second screw portion comprises a second diameter, and the section comprises a third diameter, wherein the third diameter is less than the first diameter and the second diameter. In some embodiments, the first hole comprises at least one notch, and the third radially outward facing surface comprises at least one protrusion operatively arranged to engage the at least one notch to non-rotatably connect the section with the first screw portion.

According to aspects illustrated herein, there is provided a fusion device assembly for fusion of a bone structure or joint, comprising a first screw portion, including a first distal end, a first proximal end, a first radially outward facing surface, and a first hole, a second screw portion, including a second distal end, a second proximal end, and a second radially outward facing surface, a bone graft section, including a first end slidably engaged with the first hole, a second end non-rotatably secured to the second distal end and a third radially outward facing surface, and a rod extending internally through the second screw portion, the bone graft section, and the first screw portion, wherein the rod is operatively arranged to displace the first screw portion and the second screw portion toward each other.

In some embodiments, the first screw portion further comprises threading arranged on the first radially outward facing surface, at least one flute extending from the first distal end to the first proximal end, and at least one cutting edge operatively arranged to cut through bone. In some embodiments, the first screw portion comprises a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction. In some embodiments, the second screw portion further comprises threading arranged on the second radially outward facing surface. In some embodiments, the fusion device assembly further comprises a second hole extending through the second screw portion and the bone graft section, the rod engaged with the second hole. In some embodiments, when the rod is displaced in a first circumferential direction the second screw portion and the section are displaced in a axial direction toward the first screw portion. In some embodiments, the first screw portion comprises a first diameter, the second screw portion comprises a second diameter, and the bone graft section comprises a third diameter, wherein the third diameter is less than the first diameter and the second diameter. In some embodiments, an overall length of the fusion device assembly is adjustable via the rod.

According to aspects illustrated herein, there is provided a fusion device assembly for fusion of a bone structure or joint, comprising a first screw portion, including a first distal end, a first proximal end, a first hole, a first radially outward facing surface, including a first threading, a first flute including a first cutting edge, the first cutting edge arranged proximate the first distal end and arranged to cut when the first screw portion is displaced in a first circumferential direction, and a second flute including a second cutting edge, the second cutting edge arranged proximate the first proximal end and arranged to cut when the first screw portion is displaced in a second circumferential direction, opposite the first circumferential direction, a second screw portion, including a second distal end, a second proximal end, and a second radially outward facing surface including a second threading, and a bone graft section, including a first end slidably engaged with the first hole, a second end non-rotatably secured to the second distal end, and a third radially outward facing surface.

In some embodiments, the bone material harvested by the cutting edge or edges of the tip are directed by one or more flutes to the slidable unthreaded segment of the screw or fusion device. Such bone drillings accumulate circumferentially around the unthreaded shaft component as a harvested autograft to be held and stored in that position for the purpose of fusion across a bone interface. Said graft is then capable being placed under compression according to Wolff's law by axial shortening of the unthreaded shaft component which in turn draws together the proximal and distal threaded segments of the screw or fusion device to manifest such compression of not only the harvested autograft, but also the proximate surfaces of the bone elements being fused.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Figure 1:
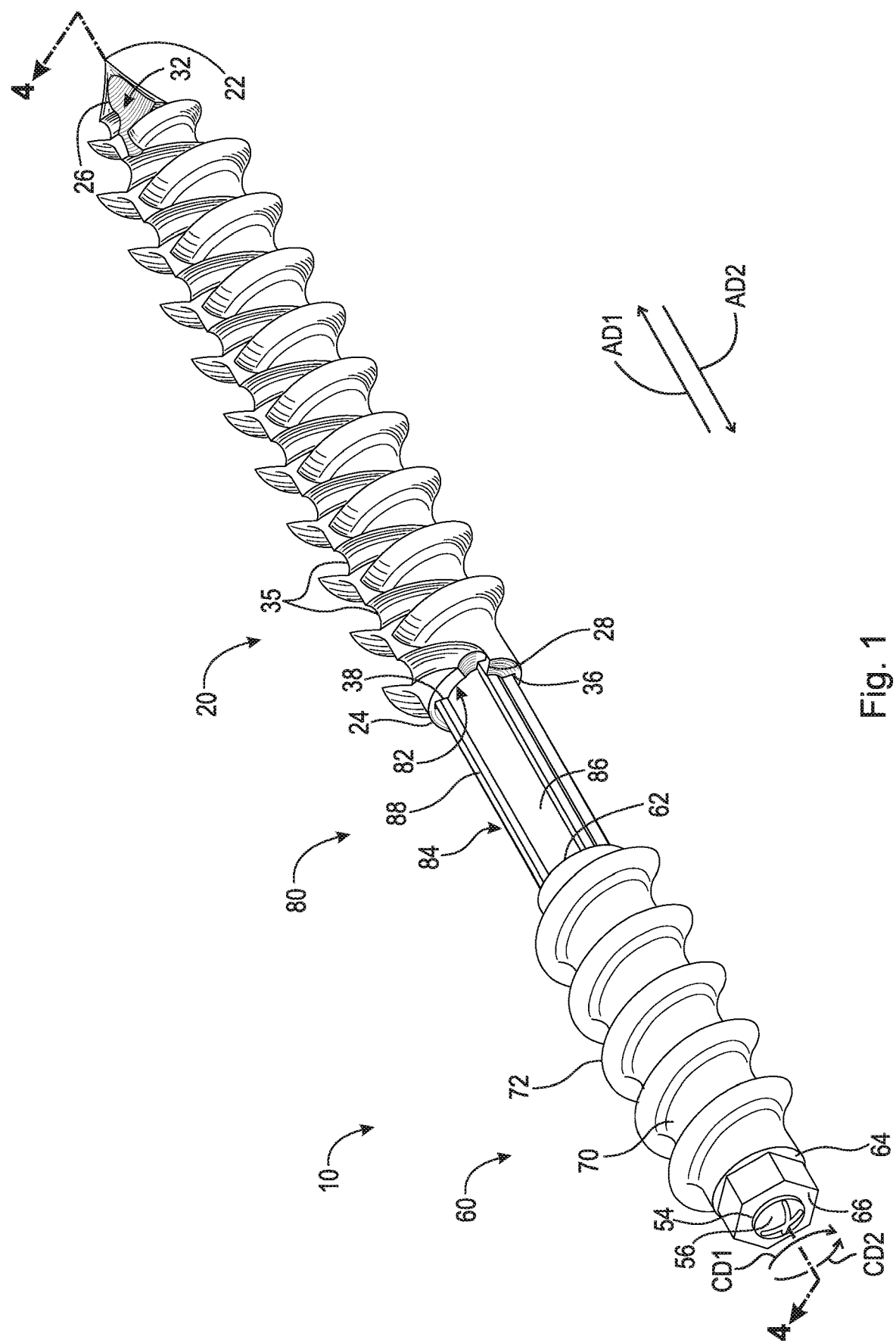
FIG. 1 is a rear perspective view of a fusion device assembly in a fully expanded state.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

By "non-rotatably connected" elements, we mean that: the elements are connected so that whenever one of the elements rotate, all the elements rotate; and relative rotation between the elements is not possible. Radial and/or axial movement of non-rotatably connected elements with respect to each other is possible, but not required.

Figure 2:
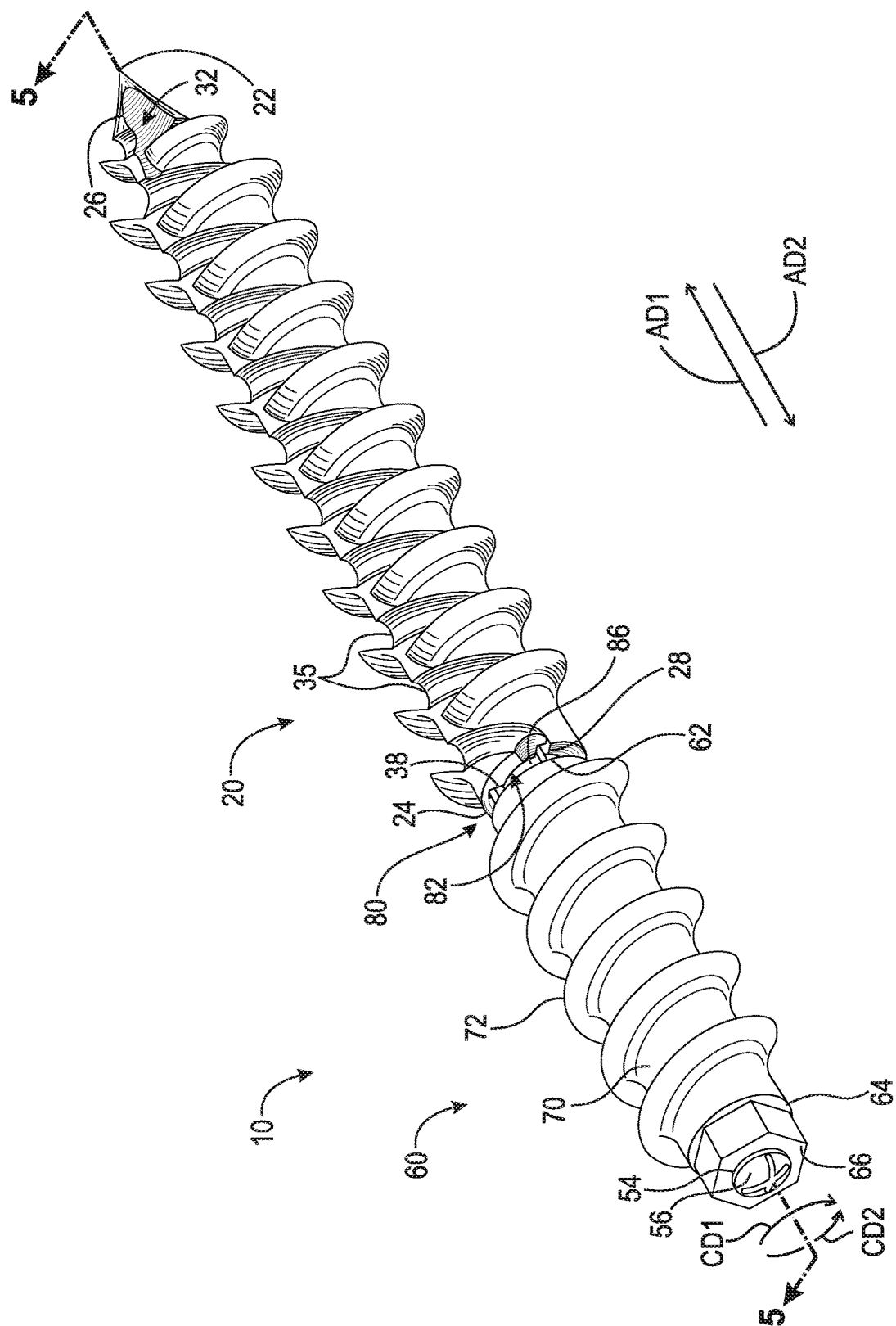
FIG. 2 is a rear perspective view of the fusion device assembly shown in FIG. 1, in a collapsed state.
Figure 3:
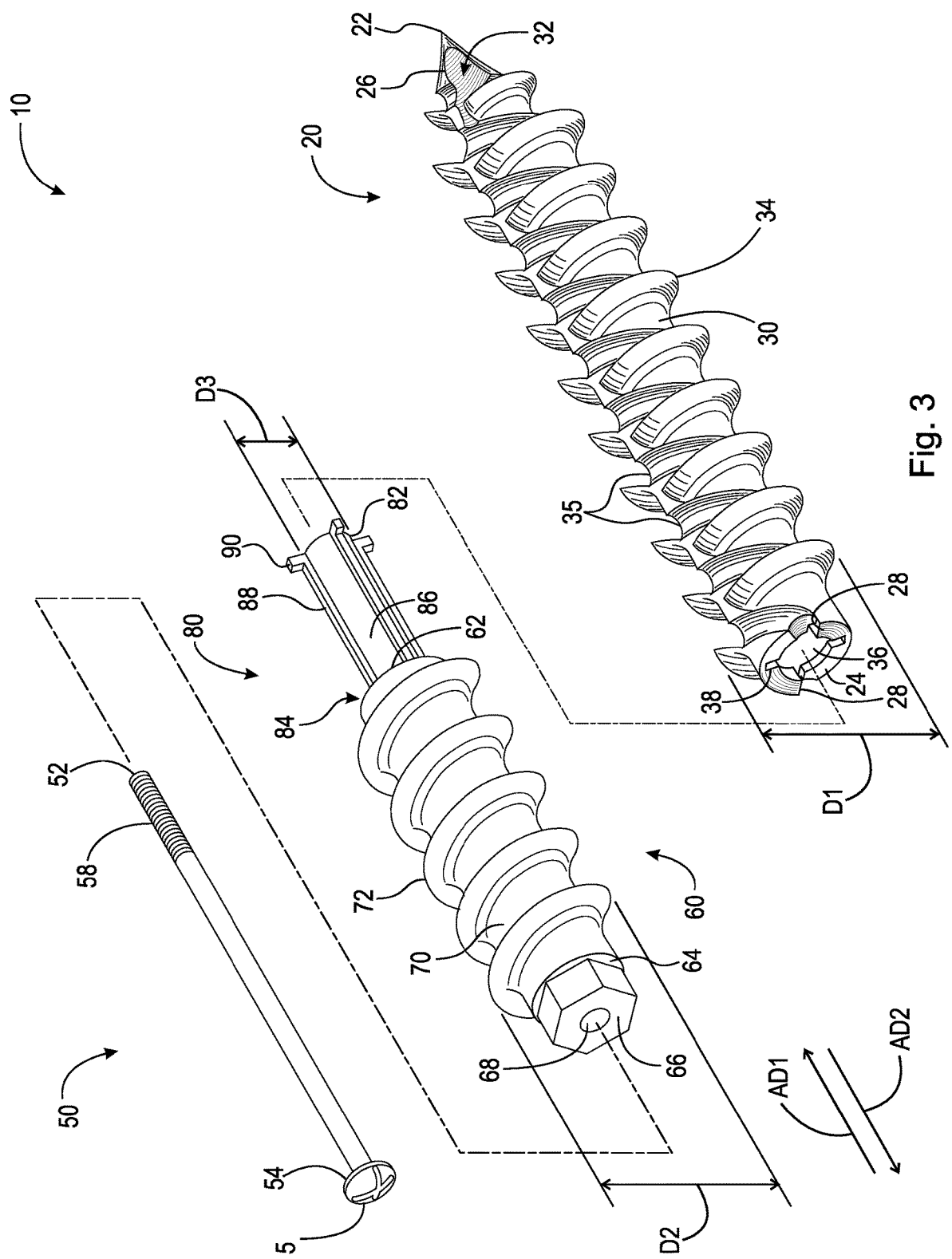
FIG. 3 is an exploded perspective view of the fusion device assembly shown in FIG. 1.
Figure 4:
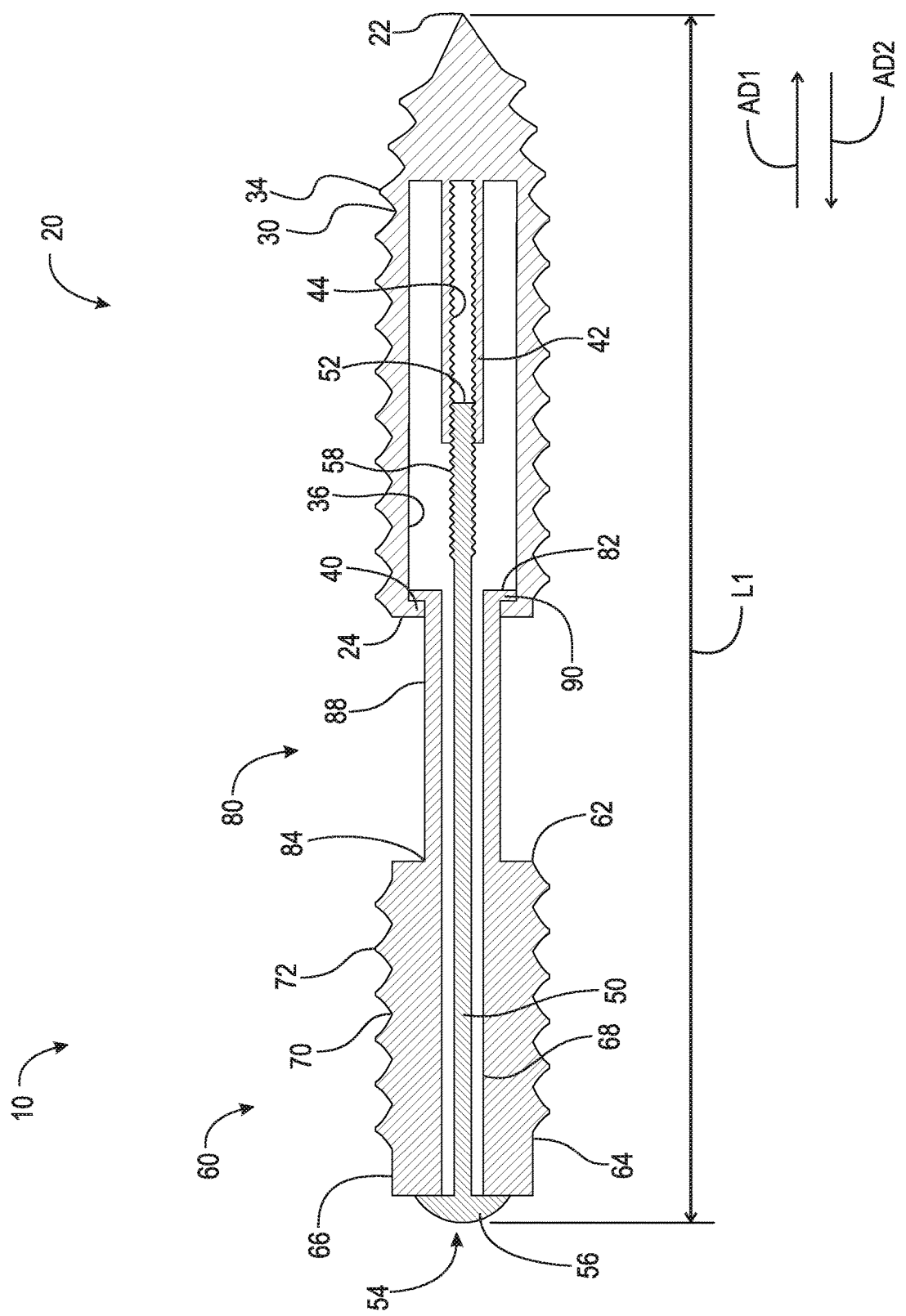
FIG. 4 is a cross-sectional view of the fusion device assembly taken generally along line 4-4 in FIG. 1.
Figure 5:
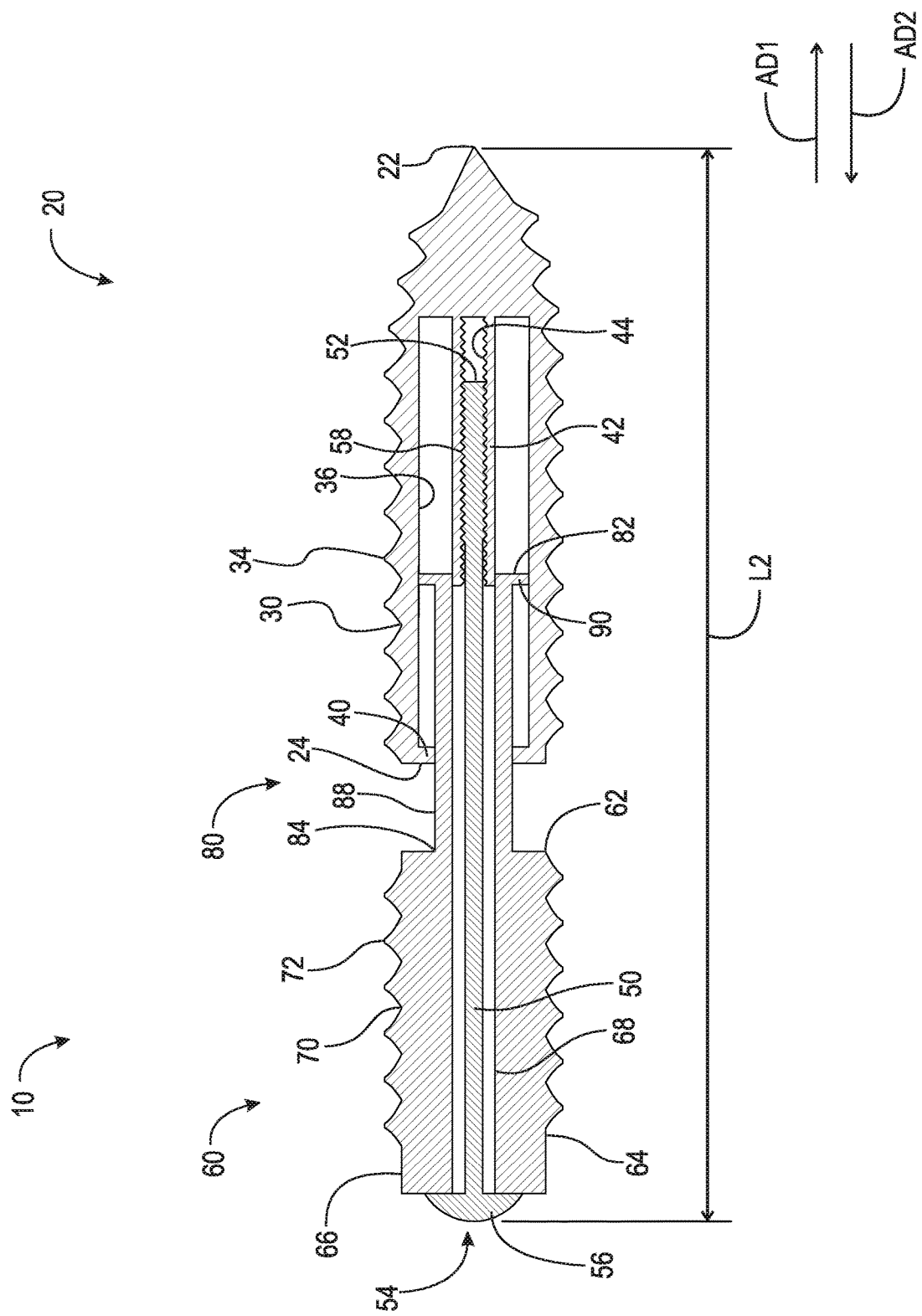
FIG. 5 is a cross-sectional view of the fusion device assembly taken generally along line 5-5 in FIG. 2.

Adverting now to the figures, FIG. 1 is a rear perspective view of fusion device assembly 10 in a fully expanded state. FIG. 2 is a rear perspective view of fusion device assembly 10 in a collapsed state. FIG. 3 is an exploded perspective view of fusion device assembly 10. FIG. 4 is a cross-sectional view of fusion device assembly 10 taken generally along line 4-4 in FIG. 1. FIG. 5 is a cross-sectional view of fusion device assembly taken generally along line 5-5 in FIG. 2. Fusion device assembly 10 generally comprises distal screw portion 20, proximal screw portion 60, bone graft section 80, and rod 50. The following description should be read in view of FIGS. 1-5.

Screw portion 20 is generally cylindrical and comprises end 22, end 24, radially outward facing surface 30, and hole 36. Hole 36 is arranged in end 24 and extends in axial direction AD1 toward end 22. In some embodiments, and as shown, hole 36 comprises one or more notches for non-rotatable connection with bone graft section 80, as will be described in greater detail below. Radially outward facing surface 30 comprises threading 34 operatively arranged to secure fusion device assembly 10 to/within bone. Radially outward facing surface 30 further comprises one or more flutes, for example, flutes 32 and 35, and one or more cutting edges or blade tips, for example, cutting edges 26 and 28. Flute 32 extends from end 22 to end 24 and is operatively arranged to displace bone material (i.e., bone shavings) from end 22 to bone graft section 80. Cutting edge 26 is arranged on or adjacent to flute 32 at end 22. As fusion device assembly 10, specifically screw portion 20, is rotated in first circumferential direction CD1, cutting edge 26 cuts through bone producing bone shavings that are drawn back to bone graft section 80 via flute 32. Flute or reverse flute 35 extends from end 24 to end 22 and is operatively arranged to displace bone material (i.e., bone shavings) from bone graft section 80 to end 22. Cutting edge 28 is arranged on or adjacent to flute 35 at end 24. As fusion device assembly 10, specifically screw portion 20, is rotated in second circumferential direction CD2, cutting edge 28 cuts through bone arranged in bone graft section 80 (i.e., that has fused) producing bone shavings that are drawn toward end 22 via flute 35. As screw portion 20 comprises cutting edges on both ends, it can be said that screw portion 20 is a self-tapping screw in both axial directions.

As best shown in FIGS. 4-5, distal screw portion 20 further comprises tube 42 fixedly secured within hole 36. Tube 42 comprises radially inward facing surface 44 operatively arranged to engage with rod 50. In some embodiments, radially inward facing surface 44 comprises threading, which is threadably engageable with threading 58 of rod 50. In some embodiments, screw portion 20 does not comprise tube 44, but rather is solid and comprises a threaded hole arranged in hole 36 into which threading 58 engages. In some embodiments, end 24 further comprises radially inward extending flange 40.

Screw portion 60 is generally cylindrical and comprises end 62, end 64, radially outward facing surface 70, head 68, and hole 68. Head 68 is fixedly secured to end 64 and is operatively arranged to engage a tool such that fusion device assembly 10 can be rotated. In some embodiments, head 68 is hexagonal. It should be appreciated that head 68 may be any geometric shape suitable for engaging with a tool for rotation, for example, square, rectangular, octagonal, triangular, etc. Radially outward facing surface 70 comprises threading 72 operatively arranged to secure fusion device assembly 10 to/within bone.

Section 80 comprises end 82, end 84, and radially outward facing surface. It should be appreciated that radially outward facing surface 86 comprises a diameter that is less than the diameter of screw portion 20 and screw portion 60. For example, screw portion 20 comprises diameter D1, screw portion 60 comprises diameter D2, and section 80 comprises diameter D3. Diameter D3 is less than diameters D1 and D2. In some embodiments, diameter D1 is equal to diameter D2. Section 80 is operatively arranged to collect bone material or bone shavings created by cutting edge 26 for bone fusion across a joint or fracture, as will be described in greater detail below. End 84 is non-rotatably connected to end 62. In some embodiments, section 80 and screw portion 60 are integrally formed. End 82 is slidably engaged with hole 36. In some embodiments, radially outward facing surface 86 comprises one or more protrusions 88 operatively arranged to engage one or more notches 38 to non-rotatably connect section 80 and screw portion 20. In some embodiments, end 82 further comprises radially outward extending flange 90. Flange 90 is operatively arranged to engage flange 40 to prevent end 82 from being removed from hole 36. In some embodiments, hole 68 extends completely through screw portion 60 and section 80. Since section 80 is slidably engaged with screw portion 20, both section 80 and screw portion 60 are axially displaceable with respect to screw portion 20. However, it should be appreciated that screw portion 20, screw portion 60, and section 80 are all non-rotatably connection (i.e., rotationally locked).

Rod 50 is generally cylindrical and comprises end 52, end 56, and head 56. Head 56 is arranged at end 54 and is operatively arranged to engage end 64, specifically head 66.

Rod 50 further comprises threading 58 arranged proximate end 52. End 52 is arranged to be fed through hole 68 and threading 58 is arranged to threadably engage with threaded hole or radially inward facing surface 44. Rod 50 is arranged radially inside of screw portion 60, section 80, and screw portion 20 which allows the overall length of fusion device assembly 10 to be shortened internally (i.e., an internal threaded rod). As rod 50, namely head 56, is rotated in circumferential direction CD1, screw portion 60 and section 80 are displaced in axial direction AD1 with respect to screw portion 20, thereby creating "compression" across the bone joint, as will be described in greater detail below. As head 56 is rotated in circumferential direction CD2, opposite circumferential direction CD1, section 80 and screw portion 60 are allowed to displace in axial direction AD2 with respect to screw portion 20. In some embodiments, as head 56 is rotated in circumferential direction CD2, section 80 and screw portion 60 are displaced in axial direction AD2 with respect to screw portion 20. As best shown in FIG. 4, when fusion device assembly 10 is in a fully expanded position, fusion device assembly 10 comprises overall length L1. As rod 50 is rotated in circumferential direction CD1, screw portion 60 and section 80 are displaced in axial direction AD1 with respect to screw portion 20, thereby decreasing the overall length of fusion device assembly 10, for example, to length L2 as shown in the collapsed position in FIG. 5.

Figure 6A:
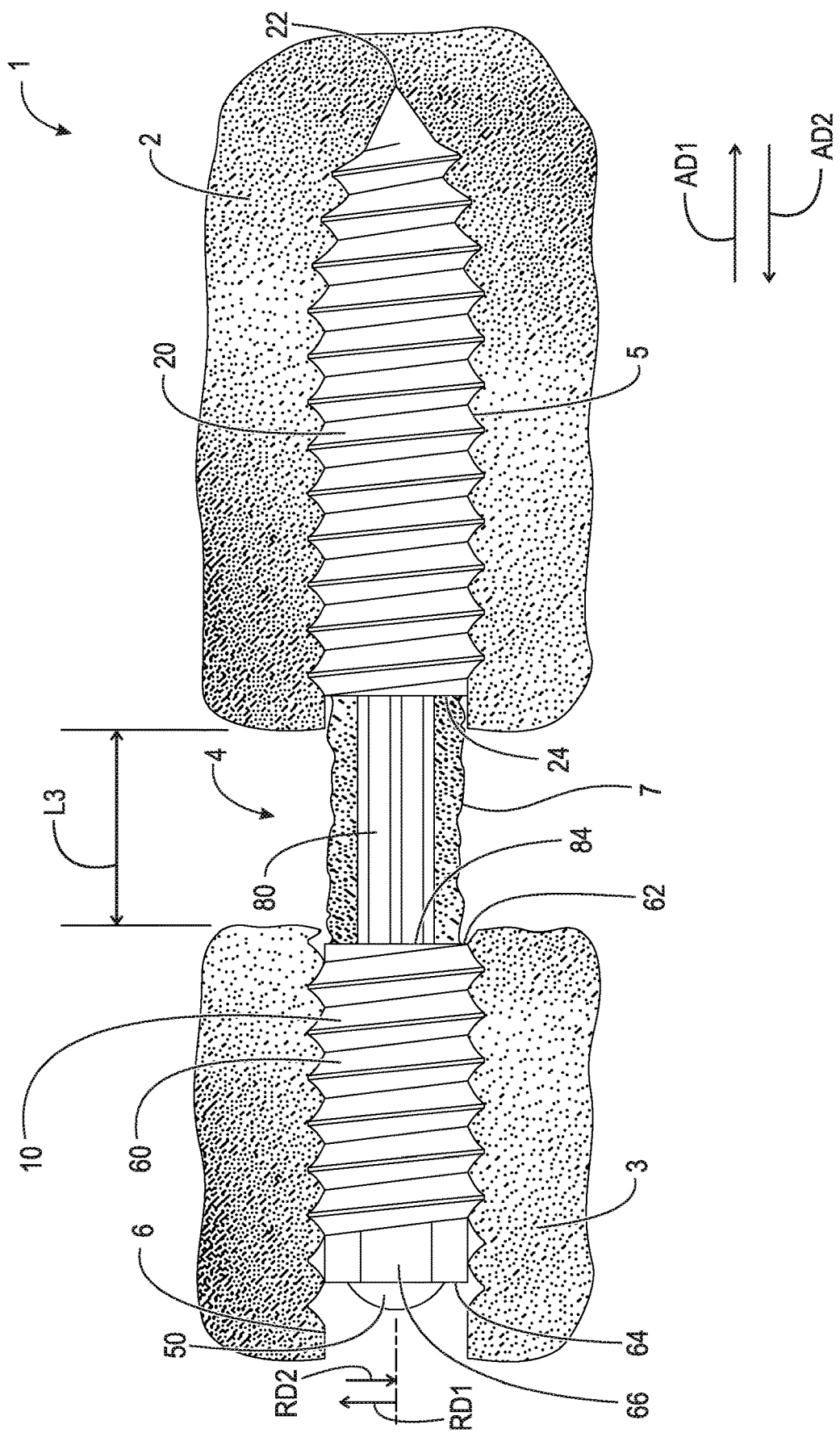
FIG. 6A is an elevational view of a fusion device assembly engaged with a bone structure in the fully expanded state; and, FIG. 6B is an elevational view of a fusion device assembly engaged with a bone structure in the collapsed state.

FIG. 6A is an elevational view of fusion device assembly 10 engaged with bone structure 1 in the fully expanded state. Bone structure 1 represents a joint or a fracture and comprises at least two sections, for example, bony anatomy 2 and bony anatomy 3. Bony anatomies 2 and 3 are separated by space 4, which comprises length L3. Fusion device 10 is arranged to reduce the length of space 4. Fusion device assembly 10 is implanted first in bony anatomy 3 and then bony anatomy 2 by screwing it in, namely in circumferential direction CD1. As previously described, when rotating fusion device assembly 10 in circumferential direction CD1, cutting edge 26 bores a hole in the bony anatomy, for example, hole 5 in bony anatomy 2 and hole 6 in bony anatomy 3. Bone drillings or shavings 7 from the cutting of the bone are then fed back through flute 32 to section 80 where they are collected. When fusion device assembly 10 is fully implanted in bone structure 1, screw portion 20 should be at least partially engaged in bony anatomy 2, screw portion 60 should be at least partially engaged with bony anatomy 3, and section 80 should be at least partially aligned with space 4.

Figure 6B:
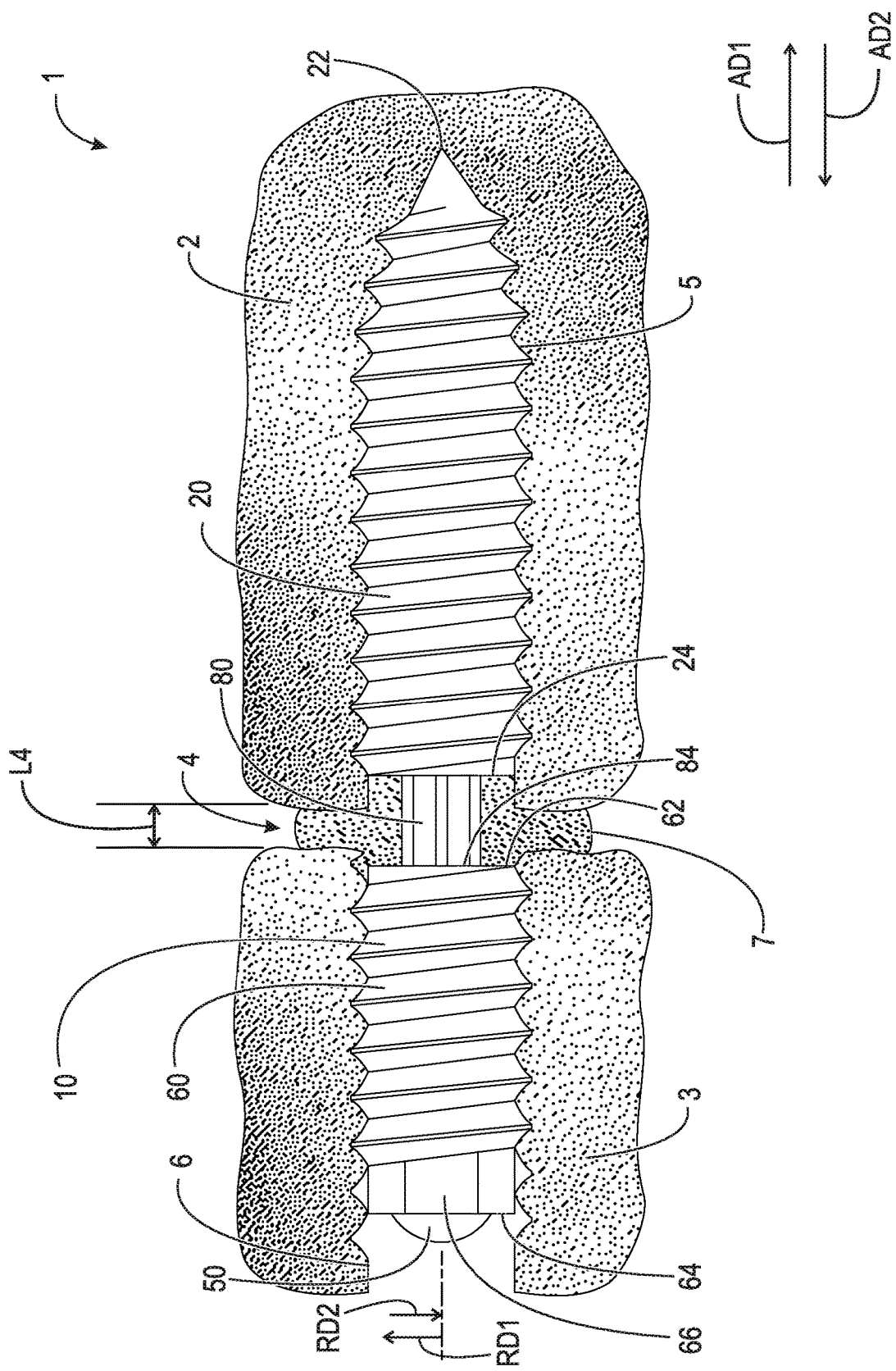

FIG. 6B is an elevational view of fusion device assembly 10 engaged with bone structure 1 in the collapsed state. Once fusion device assembly 10 is properly engaged with bone structure 1, as shown in FIG. 6B, head 66 is rotated in circumferential direction CD1 thereby displacing screw portion 60, section 80, and bony anatomy 3 in axial direction AD1 with respect to distal screw portion 20. Alternatively, as head 66 is rotated in circumferential direction CD1, screw portion 20 and bony anatomy 2 are displaced in axial direction AD2 with respect to screw portion 60, section 80, and bony anatomy 3. In both circumstances, the length of space 4 is reduced, for example to length L4, wherein bony anatomy 3 abuts or is arranged substantially proximate to bony anatomy 2. Additionally, as screw portions 20 and 60 are drawn together, ends 24 and 62 squeeze bone material or drillings 7 thereby forcing bone material 7 into contact with bony anatomies 2 and 3. The contact of the harvested bone material 7 with bony anatomies 2 and 3 completely surrounding section 80 provides for excellent bone fusion. Fusion device assembly 10 can be left in situ. Alternatively, after fusion occurs (i.e., bone material 7 has fused with bony anatomies 2 and 3 and is hardened), fusion device assembly 10 can be removed by rotating head 66 in circumferential direction CD2. As fusion device assembly 10 is rotated in circumferential direction CD2, cutting edge 28 cuts through newly fused bone and the drillings are fed through flute 35 toward end 22 allowing fusion device assembly 10 to be removed from bone structure 1. Furthermore, since cutting edge 28 will "re-bore" a hole to allow the removal of fusion device assembly 10, any lateral fusion between bony anatomies 2 and 3 will remain. This is advantageous because it allows the option of removing fusion device assembly 10 after fusion occurs, without affecting overall fusion of bone structure 1.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

LIST OF REFERENCE NUMERALS

1 Bone structure or joint
2 Bony anatomy
3 Bony anatomy
4 Space
5 Hole
6 Hole
7 Bone material or drillings
10 Fusion device assembly
20 Distal screw portion
22 End
24 End
26 Cutting edge or blade tip
28 Cutting edge or blade tip
30 Radially outward facing surface
32 Flute or flutes
34 Threading
35 Flute or flutes
36 Hole
38 Notch or notches
40 Flange
42 Tube
44 Radially inward facing surface
50 Rod
52 End
54 End
56 Head
58 Threading
60 Proximal screw portion
62 End
64 End
66 Head
68 Hole
70 Radially outward facing surface
72 Threading
80 Bone graft section
82 End
84 End
86 Radially outward facing surface
88 Protrusion or protrusions
90 Flange
AD1 Axial direction AD2 Axial direction
CD1 Circumferential direction
CD2 Circumferential direction
D1 Diameter
D2 Diameter
D3 Diameter
L1 Length
L2 Length
L3 Length
L4 Length
RD1 Radial direction
RD2 Radial direction

What is claimed is:

1. A fusion device assembly for fusion of a joint, comprising:
   a first screw portion, including:
     a first distal end;
     a first proximal end;
     a first radially outward facing surface comprising threading;
     a first hole;
     at least one flute extending from the first distal end to the first proximal end; and
     at least one cutting edge operatively arranged to cut through bone;
   a second screw portion, including:
     a second distal end;
     a second proximal end; and
     a second radially outward facing surface; and
   a section, including:
     a first end slidably engaged with the first hole;
     a second end non-rotatably secured to the second distal end; and
     a third radially outward facing surface.

2. The fusion device assembly as recited in claim 1, wherein the first screw portion comprises:
   a first flute including a first cutting edge, the first cutting edge arranged proximate the first distal end and arranged to cut when the first screw portion is displaced in a first circumferential direction; and
   a second flute including a second cutting edge, the second cutting edge arranged proximate the first proximal end and arranged to cut when the first screw portion is displaced in a second circumferential direction, opposite the first circumferential direction.

3. The fusion device assembly as recited in claim 1, wherein the second screw portion further comprises threading arranged on the second radially outward facing surface.

4. The fusion device assembly as recited in claim 1, wherein the second screw portion further comprises a head non-rotatably connected to the second proximal end.

5. The fusion device assembly as recited in claim 1, further comprising a second hole extending through the second screw portion and the section.

6. The fusion device assembly as recited in claim 5, further comprising a rod operatively arranged to extend through the second hole and engage the first screw portion.

7. The fusion device assembly as recited in claim 6, wherein when the rod is displaced in a first circumferential direction, one of the first screw portion and the second screw portion is displaced relative to the other of the first screw portion and the second screw portion.

8. The fusion device assembly as recited in claim 6, wherein when the rod is displaced in a first circumferential direction, the second screw portion and the section are displaced in an axial direction toward the first screw portion.

9. The fusion device assembly as recited in claim 1, wherein:
   the first screw portion comprises a first diameter;
   the second screw portion comprises a second diameter; and
   the section comprises a third diameter, wherein the third diameter is less than the first diameter and the second diameter.

10. The fusion device assembly as recited in claim 1, wherein:
    the first hole comprises at least one notch; and
    the third radially outward facing surface comprises at least one protrusion operatively arranged to engage the at least one notch to non-rotatably connect the section with the first screw portion.

11. A fusion device assembly for fusion of a bone structure or joint, comprising:
    a first screw portion, including:
      a first distal end;
      a first proximal end;
      a first radially outward facing surface; and
      a first hole;
    a second screw portion, including:
      a second distal end;
      a second proximal end; and
      a second radially outward facing surface;
    a bone graft section, including:
      a first end slidably engaged with the first hole;
      a second end non-rotatably secured to the second distal end; and
      a third radially outward facing surface; and
    a rod extending internally through the second screw portion, the bone graft section, and the first screw portion, wherein the rod is operatively arranged to displace the first screw portion and the second screw portion toward each other.

12. The fusion device assembly as recited in claim 11, wherein the first screw portion further comprises:
    threading arranged on the first radially outward facing surface;
    at least one flute extending from the first distal end to the first proximal end; and
    at least one cutting edge operatively arranged to cut through bone.

13. The fusion device assembly as recited in claim 11, wherein the first screw portion comprises:
    a first flute including a first cutting edge, the first cutting edge arranged proximate the first distal end and arranged to cut when the first screw portion is displaced in a first circumferential direction; and
    a second flute including a second cutting edge, the second cutting edge arranged proximate the first proximal end and arranged to cut when the first screw portion is displaced in a second circumferential direction, opposite the first circumferential direction.

14. The fusion device assembly as recited in claim 11, wherein the second screw portion further comprises threading arranged on the second radially outward facing surface.

15. The fusion device assembly as recited in claim 11, further comprising a second hole extending through the second screw portion and the bone graft section, the rod engaged with the second hole.

16. The fusion device assembly as recited in claim 11, wherein when the rod is displaced in a first circumferential direction the second screw portion and the section are displaced in an axial direction toward the first screw portion.

17. The fusion device assembly as recited in claim 11, wherein:
the first screw portion comprises a first diameter;
the second screw portion comprises a second diameter; and
the bone graft section comprises a third diameter, wherein the third diameter is less than the first diameter and the second diameter.

18. The fusion device assembly as recited in claim 11, wherein an overall length of the fusion device assembly is adjustable via the rod.

19. A fusion device assembly for fusion of a bone structure or joint, comprising:
a first screw portion, including:
  a first distal end;
  a first proximal end;
  a first hole;
  a first radially outward facing surface, including:
    a first threading;
    a first flute including a first cutting edge, the first cutting edge arranged proximate the first distal end and arranged to cut when the first screw portion is displaced in a first circumferential direction; and
    a second flute including a second cutting edge, the second cutting edge arranged proximate the first proximal end and arranged to cut when the first screw portion is displaced in a second circumferential direction, opposite the first circumferential direction;
a second screw portion, including:
  a second distal end;
  a second proximal end; and
  a second radially outward facing surface including a second threading; and
a bone graft section, including:
  a first end slidably engaged with the first hole;
  a second end non-rotatably secured to the second distal end; and
  a third radially outward facing surface.

* * * * *